United States Patent
Borup et al.

(10) Patent No.: US 9,107,433 B2
(45) Date of Patent: Aug. 18, 2015

(54) ENZYME GRANULES

(75) Inventors: Flemming Borup, Tygelsjoe (SE); Morten Mohr Hansen, Alleroed (DK); Poul Bach, Birkeroed (DK); Ole Simonsen, Soeborg (DK)

(73) Assignee: Novozymes A/S, Bagsvaerd (DK)

( * ) Notice: Subject to any disclaimer, the term of this patent is extended or adjusted under 35 U.S.C. 154(b) by 140 days.

(21) Appl. No.: 13/643,008

(22) PCT Filed: Apr. 15, 2011

(86) PCT No.: PCT/EP2011/056053
§ 371 (c)(1),
(2), (4) Date: Oct. 23, 2012

(87) PCT Pub. No.: WO2011/134809
PCT Pub. Date: Nov. 3, 2011

(65) Prior Publication Data
US 2013/0040872 A1    Feb. 14, 2013

Related U.S. Application Data

(60) Provisional application No. 61/328,234, filed on Apr. 27, 2010.

(30) Foreign Application Priority Data

Apr. 26, 2010 (EP) ..................................... 10161045

(51) Int. Cl.
| | |
|---|---|
| *C11D 3/20* | (2006.01) |
| *C11D 3/386* | (2006.01) |
| *C11D 3/04* | (2006.01) |
| *A23K 1/165* | (2006.01) |
| *C11D 17/00* | (2006.01) |
| *C11D 3/39* | (2006.01) |
| *A23K 1/00* | (2006.01) |
| *A23K 1/16* | (2006.01) |
| *A23K 1/175* | (2006.01) |
| *C12N 9/00* | (2006.01) |
| *C12N 9/98* | (2006.01) |
| *C12N 11/00* | (2006.01) |

(52) U.S. Cl.
CPC ............... *A23K 1/1653* (2013.01); *A23K 1/002* (2013.01); *A23K 1/004* (2013.01); *A23K 1/1609* (2013.01); *A23K 1/1634* (2013.01); *A23K 1/175* (2013.01); *C11D 3/38609* (2013.01); *C11D 3/38627* (2013.01); *C11D 3/38645* (2013.01); *C11D 3/38672* (2013.01); *C11D 3/39* (2013.01); *C11D 17/0039* (2013.01); *C12N 9/00* (2013.01); *C12N 9/98* (2013.01); *C12N 11/00* (2013.01)

(58) Field of Classification Search
CPC ........... C11D 3/38609; C11D 3/38627; C11D 3/38645; C11D 3/38672; C11D 3/39
USPC .......... 510/305, 320, 349, 392, 441, 367, 372
See application file for complete search history.

(56) References Cited

U.S. PATENT DOCUMENTS

| | | |
|---|---|---|
| 2004/0033927 A1 | 2/2004 | Simonsen |
| 2006/0073193 A1 | 4/2006 | Marcussen |
| 2006/0247149 A1 | 11/2006 | Bach |
| 2007/0082838 A1 | 4/2007 | De et al. |
| 2009/0291483 A1* | 11/2009 | Bach ............................ 435/187 |

FOREIGN PATENT DOCUMENTS

| | | |
|---|---|---|
| WO | 99/32595 A1 | 7/1999 |
| WO | 99/37746 A1 | 7/1999 |
| WO | 00/01793 A1 | 1/2000 |
| WO | 03/055967 A1 | 7/2003 |
| WO | 2004/003188 A2 | 1/2004 |
| WO | 2004/067739 A2 | 8/2004 |
| WO | 2006/034710 A1 | 4/2006 |
| WO | 2007/044968 A2 | 4/2007 |

* cited by examiner

*Primary Examiner* — Gregory R Delcotto
(74) *Attorney, Agent, or Firm* — Kelly Reynolds

(57) ABSTRACT

The stability of enzymes in a powder detergent can be very significantly improved by the combination of four measures: Addition of reducing agent/peroxide decomposing catalyst/antioxidant to the core or the coating; Addition of a multivalent cation to the core; Addition of an acidic buffer to the core or to the coating; Applying a salt coating onto the core.

10 Claims, No Drawings

US 9,107,433 B2

ENZYME GRANULES

CROSS-REFERENCE TO RELATED APPLICATIONS

This application is a 35 U.S.C. 371 national application of PCT/EP2011/056053 filed Apr. 15, 2011, which claims priority or the benefit under 35 U.S.C. 119 of European application no. 10161045.9 filed Apr. 26, 2010 and U.S. provisional application No. 61/328,234 filed Apr. 27, 2010, the contents of which are fully incorporated herein by reference.

FIELD OF THE INVENTION

The present invention relates to granules comprising an enzyme-containing core surrounded by a protective coating and to their use in granular (or powder) detergents. More particularly, it relates to enzyme granules with improved stability in powder detergents.

BACKGROUND OF THE INVENTION

Enzymes in the form of granules are commonly added to powder detergents, to improve the detergency. It is known in the art to incorporate enzymes into granules, to incorporate stabilizers into such granules and to surround the granules with a protective coating in order to protect the enzymes against inactivation caused by aggressive materials in the environment, e.g. to improve the storage stability of the enzyme when the granules are added to a granular detergent.

Thus, coated enzyme granules are disclosed in WO 00/01793, WO 2004/003188 (US 2004/033927), WO 2004/067739, WO 99/32595, WO 2006/034710 (US 2006/073193) and WO 2007/044968. WO 99/37746 discloses a multi-layer detergent tablet.

SUMMARY OF THE INVENTION

The inventors have found that the stability of enzymes in a powder detergent can be very significantly improved by the combination of four measures:
 Addition of a reducing agent, a peroxide decomposing catalyst or an antioxidant to the core or the coating
 Addition of a multivalent cation to the core
 Addition of an acidic buffer to the core or to the coating
 Applying a salt coating onto the core.

The inventors have found that a combination of these four measures results in a synergistic improvement of the storage stability of the enzyme activity in the granules. Accordingly, the invention provides a granule comprising a core and a protective coating, wherein:
 a) the core comprises an enzyme, and
 b) the core and/or the coating comprises a reducing agent or a peroxide decomposing catalyst or an antioxidant, and
 c) the core comprises a salt of a multivalent cation, and
 d) the core and/or the coating comprises an acidic buffer component, and
 e) the coating comprises a salt.

Furthermore, the invention provides a surfactant and the granule.

DETAILED DESCRIPTION OF THE INVENTION

Core

The core comprises the enzyme and the salt of a multivalent cation, and it may also comprise the reducing agent/antioxidant/peroxide decomposing catalyst and/or the acidic buffer component, typically as a homogenous blend. The blend may also include binders (such as synthetic polymer, wax, fat, or carbohydrate). The blend may further include additional materials such as fillers, fibre materials (cellulose or synthetic fibres), stabilizing agents, solubilising agents, suspension agents, viscosity regulating agents, light spheres, plasticizers, salts, lubricants and fragrances.

The core can be prepared by granulating the blend, e.g. by use of granulation techniques including: crystallisation, precipitation, pan-coating, fluid bed coating, fluid bed agglomeration, rotary atomization, extrusion, prilling, spheronization, size reduction methods, drum granulation, and/or high shear granulation.

The core may consist of an inert particle with the blend absorbed into it, or with the blend applied on to the surface e.g. via fluid bed coating.

The core particle may have a diameter of 20-2000 µm, particularly 50-1500 µm, 100-1500 µm or 250-1200 µm.

Enzyme

The core of the granule comprises an enzyme, e.g. an amylase, a carbohydrase, a protease, a lipase, a cellulase, an oxidoreductase, a mannanase or a pectate lyase.

The granules of the invention typically include between about 0.005 to about 500 mg/g on a dry weight basis of the enzyme component relative to the core (as active enzyme protein). For instance, the amount of enzyme in embodiments of the invention comprises about 0.05 to 300 mg/g, about 0.1 to 250 mg/g, about 0.5 to 200 mg/g, about 0.5 to 200 mg/g, about 1.0 to 150 mg/g in the granule, or about 5.0 to 150 mg/g relative to the core.

Amylase

The amylase may be an α-amylase obtained from Bacillus, e.g. B. subtilis and B. licheniformis, in particular the amylase from a special strain of B. licheniformis, described in more detail in GB 1,296,839.

Examples of useful amylases are described in WO 94/02597, WO 94/18314, WO 1995/010603, WO 1995/026397, WO 96/23873, WO 97/43424, and WO 00/60060, WO 2001/066712, WO 2006/002643, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444.

In a particular embodiment the alpha-amylase is derived from Bacillus sp. strains NCIB 12289, NCIB 12512, NCIB 12513 and DSM 9375. Especially preferred are the alpha-amylases shown in SEQ ID NOS 1 and 2 of WO 95/26397.

Commercially available amylases are NATALASE™, STAINZYME™, STAINZYME PLUS™, TERMAMYL™ ULTRA, DURAMYL™, TERMAMYL™, FUNGAMYL™ and BAN™ (Novozymes A/S), RAPIDASE™, PURASTAR™ and PURASTAR OXAM™ (from Genencor International Inc.).

Protease

Suitable proteases include those of animal, vegetable or microbial origin. Microbial origin is preferred. Chemically modified or protein engineered mutants are included. The protease may be a serine protease or a metalloprotease, preferably an alkaline microbial protease or a trypsin-like protease. Examples of alkaline proteases are subtilisins, especially those derived from Bacillus, e.g., subtilisin Novo, subtilisin Carlsberg, subtilisin 309, subtilisin 147 and subtilisin 168 (described in WO 89/06279). Examples of trypsin-like proteases are trypsin (e.g., of porcine or bovine origin) and the Fusarium protease described in WO 89/06270 and WO 94/25583.

Examples of useful proteases are the variants described in WO 92/19729, WO 98/20115, WO 98/20116, and WO 98/34946, especially the variants with substitutions in one or more of the following positions: 27, 36, 57, 76, 87, 97, 101, 104, 120, 123, 167, 170, 194, 206, 218, 222, 224, 235, and 274.

Preferred commercially available protease enzymes include Alcalase™, Savinase™, Primase™, Duralase™, Esperase™, and Kannase™ (Novozymes A/S), Maxatase™, Maxacal™, Maxapem™, Properase™, Purafect™, Purafect OxP™, FN2™, and FN3™ (Genencor International Inc.).

Lipase

The lipase may be *Thermomyces lanuginosus* lipase (TLL, shown as SEQ ID NO: 2 in WO 2009/109500), *Alcaligenes* sp. lipase, *Achromobacter* sp. lipase, *Burkholderia cepacia* lipase, *Pseudomonas stutzeri* lipase, or it may be a variant which has an amino sequence with at least 80% identity to one of these, particularly at least 85%, at least 90%, at least 95% or at least 98% identity.

Examples of TLL homologues are described in WO 1992/005249, Lipolase Ultra), WO0060063, WO9707202, WO0032758, WO02055679, WO04099400, WO07087508 and WO 2009/109500. Commercial lipases include the following products of Novozymes A/S: Novozym™ 435, Novozym 735, Lipozyme™ RM, Novozym 388, Lipolase Ultra™, Lipex™, Lipoprime™, Lipolase™, Lipoclean™ and Lipolex™.

Cellulase

Suitable cellulases include complete cellulases or mono-component endoglucanases of bacterial or fungal origin. Chemically or genetically modified mutants are included. The cellulase may for example be a mono-component or a mixture of mono-component endo-1,4-beta-glucanase often just termed endoglucanases (EC 3.2.1.4). Some xyloglucanases may also have endoglucanase activity and are also considered as suitable cellulases in the present invention. Suitable cellulases are disclosed in U.S. Pat. No. 4,435,307, which discloses fungal cellulases produced from *Humicola insolens*. Especially suitable cellulases are the cellulases having textile care benefits. Examples of such cellulases are cellulases described in European patent application No. 0 495 257.

Suitable mono-component endoglucanases may be obtained from one or more of the following species *Exidia glandulosa, Crinipellis scabella, Fomes fomentarius, Spongipellis* sp., *Rhizophlyctis rosea, Rhizomucor pusillus, Phycomyces nitens,* and *Chaetostylum fresenii, Diplodia gossypina, Microsphaeropsis* sp., *Ulospora bilgramii, Aureobasidium* sp., *Macrophomina phaseolina, Ascobolus stictoides, Saccobolus dilutellus, Peziza, Penicillium verruculosum, Penicillium chrysogenum,* and *Thermomyces verrucosus, Trichoderma reesei* aka *Hypocrea jecorina, Diaporthe syngenesia, Colletotrichum lagenarium, Xylaria hypoxylon, Nigrospora* sp., *Nodulisporum* sp., and *Poronia punctata, Cylindrocarpon* sp., *Nectria pinea, Volutella colletotrichoides, Sordaria fimicola, Sordaria macrospora, Thielavia thermophila, Syspastospora boninensis, Cladorrhinum foecundissimum, Chaetomium murorum, Chaetomium virescens, Chaetomium brasiliensis, Chaetomium cunicolorum, Myceliophthora thermophila, Gliocladium catenulatum, Scytalidium thermophila, Acremonium* sp *Fusarium solani, Fusarium anguioides, Fusarium poae, Fusarium oxysporum* ssp. *lycopersici, Fusarium oxysporum* ssp. *passiflora, Humicola nigrescens, Humicola grisea, Fusarium oxysporum, Thielavia terrestris* or *Humicola insolens*. One preferred endoglucanase is disclosed in WO 96/29397 as SEQ ID NO: 9 (hereby incorporated by reference) or an enzyme with at least 70% identity thereto and variants thereof as disclosed in Example 1 of WO 98/12307. Another preferred endoglucanase is disclosed in WO 91/017243 (SEQ ID NO:2) or endoglucanases variants as disclosed in WO 94/007998.

Endoglucanases with an anti-redeposition effect may be obtained from fungal endoglucanases lacking a carbohydrate-binding module (CBM) from a number of bacterial sources. Some sources are *Humicola insolens, Bacillus* sp. deposited as DSM 12648, *Bacillus* sp. KSMS237 deposited as FERM P-16067, *Panibacillus polymyxa,* and *Panibacillus pabuli*. Specific anti-redeposition endoglucanase are disclosed in WO 91/17244 (FIG. 14) (hereby incorporated by reference), WO 2002/099091 position 1-773 of SEQ ID NO: 2 (hereby incorporated by reference), WO 04/053039 SEQ ID NO: 2 (hereby incorporated by reference), JP 2000210081 position 1 to 824 of SEQ ID NO: 1 (hereby incorporated by reference).

Xyloglucanases with an anti-redeposition effect may be obtained from a number of bacterial sources. Some sources are *Bacillus licheniformis, Bacillus agaradhaerens,* (WO 99/02663) *Panibacillus polymyxa,* and *Panibacillus pabuli* (WO01/62903). Suitable variants of xyloglucasnes are also described in PCT/EP2009/056875. A commercially available xyloglucanase is Whitezyme® (Novozymes A/S).

Commercially available cellulases include Celluclast® produced from *Trichoderma reesei*, Celluzyme® produced from *Humicola insolens*. Commercially available endoglucanases are Carezyme®, Renozyme®, Endolase® and Celluclean® (Novozymes A/S), and KAC-500(B)™ (Kao Corporation) and Clazinase™, Puradax™ EG L and Puradax HA (Danisco A/S).

Pectate Lyase

The pectate lyase may be a wild-type enzymes derived from *Bacillus*, particularly *B. lichemiformis* or *B. agaradhaerens*, or a variant derived of these, e.g. as described in U.S. Pat. No. 6,124,127 (NZ 5543), WO 1999/027083 (NZ 5377), WO 1999/027084 (NZ 5378), WO 2002/006442 (NZ 10044), WO 2002/092741 (NZ 10171), or WO 2003/095638 (NZ 10190).

Mannanase

The mannanase may be an alkaline mannanase of Family 5 or 26. It may be a wild-type from *Bacillus* or *Humicola*, particularly *B. agaradhaerens, B. licheniformis, B. halodurans, B. clausii,* or *H. insolens*. Suitable mannanases are described in WO 1999/064619 (NZ 5440).

Reducing Agent, Peroxide Decomposing Catalyst and/or Antioxidant

The granule contains a reducing agent, a peroxide decomposing catalyst and/or an antioxidant (a molecule capable of slowing or preventing the oxidation of other molecules) in the core and/or in the coating. Examples are sulfites, thiosulfates, erythorbates, ascorbates and nitrites, e.g. as salts of alkali metals and earth alkali metals. Other suitable materials are methionine, cysteine, propyl gallate, tert-butyl hydroquinone, tocopherols, thiodipropionic acid, butylated hydroxytoluene (BHT), butylated hydroxyanisol (BHA) or tannic acid.

Further suitable examples are transition metals as reducing agents and/or peroxide decomposing catalysts like e.g. V, Co, Mn and Fe, typically as salts, e.g. sulfate-, acetate-, nitrate or chloride-salts or oxides, e.g. $FeSO_4$, $FeCl_3$, $CoSO_4$, $MnSO_4$ or $MnO_2$. Water soluble salts of the transition metals are preferred. As peroxide decomposing catalysts also an enzyme can be used, e.g. catalase.

The amount of the antioxidant, peroxide decomposing catalyst or reducing agent may be at least 0.1% by weight relative to the core, particularly at least 0.2%, at least 0.5%, at least 1%, or at least 1% The amount may be at most 10% by weight relative to the core, particularly at most 5%, at most 4%, at most 3% or at most 2%. Here, the amount of a salt is calculated in anhydrous form. Peroxide decomposing catalysts can be efficient in even lower concentrations, e.g. at least 0.001%, or at least 0.01%; the amount may be at most 5% or at most 1%.

Salt of a Multivalent Cation

The granule contains a salt of a multivalent cation in the core, particularly a divalent or trivalent cation, e.g. a salt of Mg, Zn, Cu, Mn, Ca or Al. The salt may include an organic or inorganic anion such as sulfate, chloride or acetate. Particular salts include magnesium sulfate and zinc sulfate, e.g. magnesium sulfate heptahydrate.

The salt may be used in an amount of at least 0.1% by weight of the core, particularly at least 0.5% by weight, e.g. at least 1% by weight. The amount may be at most 15%, 10% or 5%. The percentage indicates the amount of the salt in anhydrous form.

The multivalent cation may be used in an amount of at least 0.02% by weight of the core, particularly at least 0.1% by weight, e.g. at least 0.2% by weight. The amount may be at most 6%, at most 4% or at most 2%. The percentage indicates the amount of the multivalent cation. Acidic buffer component The granule contains an acidic buffer component (acidic buffering agent) in the core or the coating. The amount may be at least 0.1 by weight of the core, particularly at least 1% by weight. The amount is typically at most 10% by weight of the core, particularly at most 5% by weight. The percentage indicates the amount in anhydrous form.

The acidic buffer component has a pH below 7 when measured as a 1% by weight aqueous solution (or alternatively a 10% solution). The acidic buffer component may have a pH of 1 to below 7, e.g. a pH of 3 to below 7, particularly a pH of 4 to 5. The acidic buffer component is typically a mixture comprising a weak acid and the corresponding base; it is at least partly in its acid form Furthermore the acidic buffer component has a pKa from 2 to 9, in particular a $pK_a$ from 4 to 9, in particular a $pK_a$ from 5 to 8, in particular a $pK_a$ from 2 to 6, in particular a $pK_a$ from 2 to 5, in particular a $pK_a$ from 2 to 4, in particular a $pK_a$ from 5 to 7. To utilize most of the potential buffer capacity the pH of an aqueous solution is in general below the $pK_a$.

Particularly suitable acidic buffer components are salts of $H_3PO_4$ e.g. $NaH_2PO_4$, $KH_2PO_4$, and $Ca(H_2PO_4)_2$, polyphosphates e.g. sodium hexametaphosphate, polyacrylic acid and partly neutralized polyacrylic acid and co-polymers thereof, simple organic acids (less than 10 carbon atoms e.g. 6 or less carbon atoms) such as citric acid and salts thereof such as hydrogen citrate, e.g. disodium hydrogen citrate, malonic, succinic, glutaric, adipic acid.

In a particular embodiment the acidic buffer components are selected from the group consisting of polyacrylic acid and partly neutralized polyacrylic acid and co-polymers thereof, citric acid and $Na_3$-citrate.

Salt Coating

The granule comprises a core surrounded by at least one coating. The coating may comprise at least 60% by weight w/w of a salt, e.g. at least 65%, at least 70%, at least 75%, at least 80%, at least 85%, at least 90%, at least 95% or at least 99% by weight w/w.

The coating may be applied in an amount of at least 5% by weight of the core, e.g. at least 10%, 10% or 15%. The amount may be at most 70%, 50%, 40% or 30%.

To provide acceptable protection, the salt coating is preferably at least 1 µm thick, particularly at least 2 µm, at least 4 µm or at least 8 µm. The thicker the coating the more time consuming and expensive it gets to produce the granule. In a particular embodiment the thickness of the salt coating is below 100 µm. In a more particular embodiment the thickness of the salt coating is below 60 µm. In an even more particular embodiment the total thickness of the salt coating is below 40 µm.

The coating should encapsulate the core unit by forming a substantially continuous layer. A substantially continuous layer is to be understood as a coating having few or no holes, so that the core unit it is encapsulating has few or none uncoated areas. The layer or coating should in particular be homogenous in thickness. The salt may be added from a salt solution where the salt is completely dissolved or from a salt suspension wherein the fine particles is less than 50 µm, such as less than 10 µm or less than 5 µm.

The salt coating is especially effective if it is applied in a fluid bed under relatively high humidity conditions.

The reducing agent/antioxidant/peroxide decomposing catalyst may be part of the salt coating, either as a homogeneous part of the entire salt coating, or as part of this coating, e.g. only as an inner layer of salt and/antioxidant/peroxide decomposing catalyst. Using e.g. $FeSO_4$ as a reducing agent/peroxide decomposing catalyst may induce a color change as the metal is oxidized, which can be hidden by having the component as an inner layer.

The salt coating can further contain other materials as known in the art, e.g. fillers, antisticking agents, pigments, dyes, plasticizers and/or binders, such as titanium dioxide, kaolin, calcium carbonate or talc.

Salts

The salt coating may comprise a single salt or a mixture of two or more salts. The salt may be water soluble, in particular having a solubility at least 0.1 grams in 100 g of water at 20° C., preferably at least 0.5 g per 100 g water, e.g. at least 1 g per 100 g water, e.g. at least 5 g per 100 g water.

The salt may be an inorganic salt, e.g. salts of sulfate, sulfite, phosphate, phosphonate, nitrate, chloride or carbonate or salts of simple organic acids (less than 10 carbon atoms e.g. 6 or less carbon atoms) such as citrate, malonate or acetate. Examples of cations in these salt are alkali or earth alkali metal ions, the ammonium ion or metal ions of the first transition series, such as sodium, potassium, magnesium, calcium, zinc or aluminium. Examples of anions include chloride, bromide, iodide, sulfate, sulfite, bisulfite, thiosulfate, phosphate, monobasic phosphate, dibasic phosphate, hypophosphite, dihydrogen pyrophosphate, tetraborate, borate, carbonate, bicarbonate, metasilicate, citrate, malate, maleate, malonate, succinate, lactate, formate, acetate, butyrate, propionate, benzoate, tartrate, ascorbate or gluconate. In particular alkali- or earth alkali metal salts of sulfate, sulfite, phosphate, phosphonate, nitrate, chloride or carbonate or salts of simple organic acids such as citrate, malonate or acetate may be used. Specific examples include $NaH_2PO_4$, $Na_2HPO_4$, $Na_3PO_4$, $(NH_4)H_2PO_4$, $K_2HPO_4$, $KH_2PO_4$, $Na_2SO_4$, $K_2SO_4$, $KHSO_4$, $ZnSO_4$, $MgSO_4$, $CuSO_4$, $Mg(NO_3)_2$, $(NH_4)_2SO_4$, sodium borate, magnesium acetate and sodium citrate.

The salt may be in anhydrous form, or it may be a hydrated salt, i.e. a crystalline salt hydrate with bound water(s) of crystallization, such as described in WO 99/32595. Specific examples include anhydrous sodium sulfate ($Na_2SO_4$), anhydrous magnesium sulfate ($MgSO_4$), magnesium sulfate heptahydrate ($MgSO_4(7H_2O)$), zinc sulfate heptahydrate ($ZnSO_4(7H_2O)$), sodium phosphate dibasic heptahydrate ($Na_2HPO_4(7H_2O)$), magnesium nitrate hexahydrate ($Mg(NO_3)_2(6H_2O)$), sodium borate decahydrate, sodium citrate dihydrate and magnesium acetate tetrahydrate.

The salt in the coating may have a constant humidity at 20° C. above 60%, particularly above 70%, above 80% or above 85% by weight, or it may be another hydrate form of such a salt (e.g. anhydrate). The salt coating may be according to WO 00/01793, which is hereby incorporated by reference.

Specific examples of suitable salts are NaCl ($CH_{20°\,C.}$=76% by weight), $Na_2CO_3$ ($CH_{20°\,C.}$=92% by weight), $NaNO_3$ ($CH_{20°\,C.}$=73% by weight), $Na_2HPO_4$ ($CH_{20°\,C.}$=95% by weight), $Na_3PO_4$ ($CH_{25°\,C.}$=92% by weight), $NH_4Cl$ ($CH_{20°\,C.}$=79.5% by weight), $(NH_4)_2HPO_4$ ($CH_{20°\,C.}$=93.0% by weight), $NH_4H_2PO_4$ ($CH_{20°\,C.}$=93.1% by weight), $(NH_4)_2SO_4$ ($CH_{20°\,C.}$=81.1% by weight), KCl ($CH_{20°\,C.}$=85% by weight), $K_2HPO_4$ ($CH_{20°\,C.}$=92% by weight), $KH_2PO_4$ ($CH_{20°\,C.}$=96.5% by weight), $KNO_3$ ($CH_{20°\,C.}$=93.5% by weight), $Na_2SO_4$ ($CH_{20°\,C.}$=93% by weight), $K_2SO_4$ ($CH_{20°\,C.}$=98% by weight), $KHSO_4$ ($CH_{20°\,C.}$=86% by weight), $MgSO_4$ ($CH_{20°\,C.}$=90% by weight), $ZnSO_4$ ($CH_{20°\,C.}$=90% by weight) and sodium citrate ($CH_{25°}$=86% by weight).

In a particular embodiment the salt is selected from the group consisting of NaCl, $Na_2CO_3$, $NaNO_3$, $Na_2HPO_4$, $Na_3PO_4$, $NH_4Cl$, $(NH_4)_2HPO_4$, $NH_4H_2PO_4$, $(NH_4)_2SO_4$, KCl, $K_2HPO_4$, $KH_2PO_4$, $KNO_3$, $Na_2SO_4$, $K_2SO_4$, $KHSO_4$, $MgSO_4$, $ZnSO_4$, NaCl and sodium citrate or mixtures thereof. In a more particular embodiment the salt is selected from the group consisting of NaCl, $Na_2CO_3$, $NaNO_3$, $Na_2HPO_4$, $Na_3PO_4$, $NH_4Cl$, $(NH_4)_2HPO_4$, $NH_4H_2PO_4$, $(NH_4)_2SO_4$, KCl, $K_2HPO_4$, $KH_2PO_4$, $KNO_3$, $Na_2SO_4$, $K_2SO_4$, $KHSO_4$, NaCl and sodium citrate or mixtures thereof.

In a particular embodiment the salt comprised in the coating of the granule is selected from the group consisting of NaCl, $Na_2CO_3$, $NaNO_3$, $Na_2HPO_4$, $Na_3PO_4$, $NH_4Cl$, $(NH_4)_2HPO_4$, $NH_4H_2PO_4$, $(NH_4)_2SO_4$, KCl, $K_2HPO_4$, $KH_2PO_4$, $KNO_3$, $Na_2SO_4$, $K_2SO_4$, $KHSO_4$, $MgSO_4$, $ZnSO_4$, NaCl and sodium citrate or mixtures thereof.

Preferably the salt it applied as a solution of the salt e.g. using a fluid bed.

Optional Additional Coating

Optionally, the granule may include an additional coating on the outside of the salt coating, e.g. in an amount of at least 0.5% by weight of the core, particularly at least 1%, e.g. at most 20% or 10%. The additional coating may comprise polyethylene glycol (PEG), hydroxypropyl methyl cellulose (HPMC or MHPC), polyvinyl alcohol (PVA) or other film forming agents and can further contain fillers, antisticking agents, pigment, dye, plasticizers etc.

Other additional coatings on the inside or outside of the salt coatings may be applied as known for people skilled in the art.

Detergent Composition

The granules are particularly suited for incorporation in a granular detergent composition comprising a surfactant. Enzyme granules according to the invention result in improved storage stability of the enzyme when the granules are incorporated in a detergent, even a detergent comprising aggressive components such as a bleaching system.

The detergent composition may for example be formulated as a laundry detergent composition for hand or machine washings including a cleaning additive composition suitable for pre-treatment of stained fabrics or a fabric softener composition, or a detergent composition for use in general household hard surface cleaning operations, or a composition for hand or machine dishwashing operations.

The detergent composition of the invention may be in any convenient dry form, e.g., a bar, a tablet, a powder, a granulate or a paste. It may also be a liquid detergent, either an aqueous or non-aqueous liquid detergent.

Surfactant

The detergent composition comprises one or more surfactants, which may be non-ionic including semi-polar and/or anionic and/or cationic and/or zwitterionic. The surfactants are typically present at a level of from 0.1% to 60% by weight.

When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap.

When included therein the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl N-alkyl derivatives of glucosamine ("glucamides").

The detergent composition may comprise one or more surfactants, which may be anionic and/or cationic and/or non-ionic and/or semi-polar and/or zwitterionic, or a mixture thereof. In a particular embodiment, the detergent composition includes a mixture of one or more nonionic surfactants and one or more anionic surfactants. The surfactant(s) is typically present at a level of from about 0.1% to 60% by weight, such as about 1% to about 40%, or about 3% to about 20%, or about 3% to about 10%.

When included therein the detergent will usually contain from about 1% to about 40% by weight, such as from about 5% to about 30%, including from about 5% to about 15%, or from about 20% to about 25% of an anionic surfactant. Non-limiting examples of anionic surfactants include sulfates and sulfonates, in particular, linear alkylbenzenesulfonates (LAS), branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES, also known as alcohol ethoxysulfates or fatty alcohol ether sulfates), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfosuccinic acid or soap, and combinations thereof.

Non-limiting examples of cationic surfactants include alkyldimethylethanolamine quat (ADMEAQ), cetyltrimethylammonium bromide (CTAB), dimethyldistearylammonium chloride (DSDMAC), and alkylbenzyldimethylammonium, and combinations thereof.

When included therein the detergent will usually contain from about 0.2% to about 40% by weight of a non-ionic surfactant, for example from about 0.5% to about 30%, in particular from about 1% to about 20%, from about 3% to about 10%, such as from about 3% to about 5%, or from about 8% to about 12%. Non-limiting examples of non-ionic surfactants include alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamide (PFAM), polyhydroxy alkyl fatty acid amides, or N-acyl N-alkyl derivatives of glucosamine (glucamides, GA, or fatty acid glucamide, FAGA), as well as products available under the trade names SPAN and TWEEN, and combinations thereof.

Non-limiting examples of semipolar surfactants include amine oxides (AO) such as alkyldimethylamineoxide, N-(coco alkyl)-N,N-dimethylamine oxide and N-(tallowalkyl)-N,N-bis(2-hydroxyethyl)amine oxide, fatty acid alkanolamides and ethoxylated fatty acid alkanolamides, and combinations thereof.

Non-limiting examples of zwitterionic surfactants include betaine, alkyldimethylbetaine, and sulfobetaine, and combinations thereof.

Builder or Complexing Agent

The detergent may contain 0-65% of a detergent builder or complexing agent such as zeolite, diphosphate, triphosphate, phosphonate, carbonate, citrate, nitrilotriacetic acid, ethylenediaminetetraacetic acid, diethylenetriaminepentaacetic acid, alkyl- or alkenylsuccinic acid, soluble silicates or layered silicates (e.g. SKS-6 from Hoechst).

In a dish wash detergent, the level of builder is typically 40-65%, particularly 50-65%. The builder and/or co-builder may particularly be a chelating agent that forms water-soluble complexes with Ca and Mg. Non-limiting examples of builders include zeolites, diphosphates (pyrophosphates), triphosphates such as sodium triphosphate (STP or STPP), carbonates such as sodium carbonate, soluble silicates such as sodium metasilicate, layered silicates (e.g., SKS-6 from Hoechst), ethanolamines such as 2-aminoethan-1-ol (MEA), iminodiethanol (DEA) and 2,2',2"-nitrilotriethanol (TEA), and carboxymethylinulin (CMI), and combinations thereof.

The detergent composition may include a co-builder alone, or in combination with a builder, for example a zeolite builder. Non-limiting examples of co-builders include homopolymers of polyacrylates or copolymers thereof, such as poly(acrylic acid) (PAA) or copoly(acrylic acid/maleic acid) (PAA/PMA). Further non-limiting examples include citrate, chelators such as aminocarboxylates, aminopolycarboxylates and phosphonates, and alkyl- or alkenyl-succinic acid. Additional specific examples include 2,2',2"-nitrilotriacetic acid (NTA), etheylenediaminetetraacetic acid (EDTA), diethylenetriaminepentaacetic acid (DTPA), iminodisuccinic acid (IDS), ethylenediamine-N,N'-disuccinic acid (EDDS), methylglycinediacetic acid (MGDA), glutamic acid-N,N-diacetic acid (GLDA), 1-hydroxyethane-1,1-diylbis(phosphonic acid) (HEDP), ethylenediaminetetrakis(methylene)tetrakis (phosphonic acid) (EDTMPA), diethylenetriaminepentakis (methylene)pentakis(phosphonic acid) (DTPMPA), N-(2-hydroxyethyl)iminodiacetic acid (EDG), aspartic acid-N-monoacetic acid (ASMA), aspartic acid-N,N-diacetic acid (ASDA), aspartic acid-N-monopropionic acid (ASMP), iminodisuccinic acid (IDA), N-(2-sulfomethyl) aspartic acid (SMAS), N-(2-sulfoethyl) aspartic acid (SEAS), N-(2-sulfomethyl) glutamic acid (SMGL), N-(2-sulfoethyl) glutamic acid (SEGL), N-methyliminodiacetic acid (MIDA), α-alanine-N,N-diacetic acid (α-ALDA), serine-N,N-diacetic acid (SEDA), isoserine-N,N-diacetic acid (ISDA), phenylalanine-N,N-diacetic acid (PHDA), anthranilic acid-N,N-diacetic acid (ANDA), sulfanilic acid-N,N-diacetic acid (SLDA), taurine-N,N-diacetic acid (TUDA) and sulfomethyl-N,N-diacetic acid (SMDA), N-(hydroxyethyl)-ethylidenediaminetriacetate (HEDTA), diethanolglycine (DEG), Diethylenetriamine Penta (Methylene Phosphonic acid) (DTPMP), amino-tris(methylenephosphonic acid) (ATMP), and combinations and salts thereof. Further exemplary builders and/or co-builders are described in, e.g., WO 09/102854, U.S. Pat. No. 5,977,053.

Polymer

The detergent may comprise one or more polymers. Examples are carboxymethylcellulose, poly(vinylpyrrolidone), poly(ethylene glycol), poly(vinyl alcohol), poly(vinylpyridine-N-oxide), poly(vinylimidazole), polycarboxylates such as polyacrylates, maleic/acrylic acid copolymers and lauryl methacrylate/acrylic acid copolymers.

Bleachning System

The detergent may contain a bleaching system, which may comprise a $H_2O_2$ source such as perborate or percarbonate, which may be combined with a peracid-forming bleach activator such as tetraacetylethylenediamine or nonanoyloxybenzenesulfonate. Alternatively, the bleaching system may comprise peroxyacids of e.g. the amide, imide, or sulfone type.

Suitable bleaching system components include bleaching catalysts, photobleaches, bleach activators, sources of hydrogen peroxide such as sodium percarbonate and sodium perborates, preformed peracids and mixtures thereof. Suitable preformed peracids include, but are not limited to, peroxycarboxylic acids and salts, percarbonic acids and salts, perimidic acids and salts, peroxymonosulfuric acids and salts, for example, Oxone (R), and mixtures thereof. Non-limiting examples of bleaching systems include peroxide-based bleaching systems, which may comprise, for example, an inorganic salt, including alkali metal salts such as sodium salts of perborate (usually mono- or tetra-hydrate), percarbonate, persulfate, perphosphate, persilicate salts, in combination with a peracid-forming bleach activator. Suitable photobleaches may for example be sulfonated zinc phthalocyanine. Suitable bleach activators include 4-(dodecanoyloxy)benzenesulfonate (LOBS), 4-(decanoyloxy)benzenesulfonate, 4-(decanoyloxy)benzoate (DOBS), 4-(3,5,5-trimethylhexanoyloxy)benzenesulfonate (ISONOBS), tetraacetylethylenediamine (TAED) and 4-(nonanoyloxy) benzenesulfonate (NOBS), and/or those disclosed in WO98/17767. Alternatively, the bleaching system may comprise peroxyacids of, for example, the amide, imide, or sulfone type. The bleaching system may also comprise peracids such as 6-(phthaloylamino)percapronic acid (PAP). The bleaching system may also include a bleach catalyst. In some embodiments the bleach component may be an organic catalyst selected from the group consisting of organic catalysts having the following formulae:

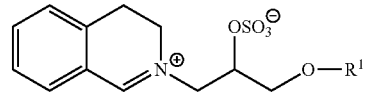

(i)

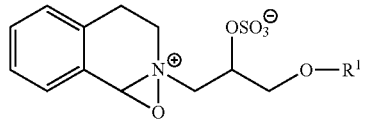

(ii)

(iii) and mixtures thereof; wherein each $R^1$ is independently a branched alkyl group containing from 9 to 24 carbons or linear alkyl group containing from 11 to 24 carbons, preferably each $R^1$ is independently a branched alkyl group containing from 9 to 18 carbons or linear alkyl group containing from 11 to 18 carbons, more preferably each $R^1$ is independently selected from the group consisting of 2-propylheptyl, 2-butyloctyl, 2-pentylnonyl, 2-hexyldecyl, n-dodecyl, n-tetradecyl, n-hexadecyl, n-octadecyl, iso-nonyl, iso-decyl, iso-tridecyl and iso-pentadecyl. Other exemplary bleaching systems are described, e.g., in WO2007/087258, WO2007/087244, WO2007/087259, WO2007/087242.Hydrotropes A hydrotrope is a compound that solubilises hydrophobic compounds in aqueous solutions (or oppositely, polar substances in a non-polar environment). Typically, hydrotropes have both hydrophilic and a hydrophobic character (so-called amphiphilic properties as known from surfactants); however the molecular structure of hydrotropes generally do not favor spontaneous self-aggregation, see e.g. review by Hodgdon and Kaler (2007), Current Opinion in Colloid & Interface Science 12: 121-128. Hydrotropes do not display a critical concentration above which self-aggregation occurs, as found for surfactants and lipids forming miceller, lamellar or other well defined meso-phases. Instead, many hydrotropes show a continuous-type aggregation process where the size of aggregates grow as concentration increases. However, many hydrotropes alter the phase behavior, stability, and colloidal properties of systems containing substances of polar and non-polar character, including mixtures of water, oil, surfactants, and polymers. Hydrotropes are classically used across industries from pharma, personal care, food, to technical applications. Use of hydrotropes in detergent compositions allow for example more concentrated formulations of surfactants (as in the process of compacting liquid detergents by removing water) without inducing undesired phenomena such as phase separation or high viscosity.

The detergent may contain 0-5% by weight, such as about 0.5 to about 5%, or about 3% to about 5%, of a hydrotrope. Non-limiting examples of hydrotropes include sodium benzene sulfonate, sodium p-toluene sulfonates (STS), sodium xylene sulfonates (SXS), sodium cumene sulfonates (SCS), sodium cymene sulfonate, amine oxides, alcohols and polyglycolethers, sodium hydroxynaphthoate, sodium hydroxynaphthalene sulfonate, sodium ethylhexyl sulfate, and combinations thereof.

Fabric Hueing Agents

The detergent compositions of the present invention may also include fabric hueing agents such as dyes or pigments which when formulated in detergent compositions can deposit onto a fabric when said fabric is contacted with a wash liquor comprising said detergent compositions thus altering the tint of said fabric through absorption/reflection of visible light. Fluorescent whitening agents emit at least some visible light. In contrast, fabric hueing agents alter the tint of a surface as they absorb at least a portion of the visible light spectrum. Suitable fabric hueing agents include dyes and dye-clay conjugates, and may also include pigments. Suitable dyes include small molecule dyes and polymeric dyes. Suitable small molecule dyes include small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof, for example as described in WO2005/03274, WO2005/03275, WO2005/03276 and EP1876226 (hereby incorporated by reference). The detergent composition preferably comprises from about 0.00003 wt % to about 0.2 wt %, from about 0.00008 wt % to about 0.05 wt %, or even from about 0.0001 wt % to about 0.04 wt % fabric hueing agent. The composition may comprise from 0.0001 wt % to 0.2 wt % fabric hueing agent, this may be especially preferred when the composition is in the form of a unit dose pouch. Suitable hueing agents are also disclosed in, e.g., WO 2007/087257, WO2007/087243.

Detergent Formulations

The enzyme granules may be included in a granular detergent formulated as described in WO09/092699, EP1705241, EP1382668, WO07/001262, U.S. Pat. No. 6,472,364, WO04/074419 or WO09/102854. Other useful detergent formulations are described in WO09/124162, WO09/124163, WO09/117340, WO09/117341, WO09/117342, WO09/072069, WO09/063355, WO09/132870, WO09/121757, WO09/112296, WO09/112298, WO09/103822, WO09/087033, WO09/050026, WO09/047125, WO09/047126, WO09/047127, WO09/047128, WO09/021784, WO09/010375, WO09/000605, WO09/122125, WO09/095645, WO09/040544, WO09/040545, WO09/024780, WO09/004295, WO09/004294, WO09/121725, WO09/115391, WO09/115392, WO09/074398, WO09/074403, WO09/068501, WO09/065770, WO09/021813, WO09/030632, WO09/015951, WO2011025615, WO2011016958, WO2011005803, WO2011005623, WO2011005730, WO2011005844, WO2011005904, WO2011005630, WO2011005830, WO2011005912, WO2011005905, WO2011005910, WO2011005813, WO2010135238, WO2010120863, WO2010108002, WO2010111365, WO2010108000, WO2010107635, WO2010090915, WO2010033976, WO2010033746, WO2010033747, WO2010033897, WO2010033979, WO2010030540, WO2010030541, WO2010030539, WO2010024467, WO2010024469, WO2010024470, WO2010025161, WO2010014395, WO2010044905, WO2010145887, WO2010142503, WO2010122051, WO2010102861, WO2010099997, WO2010084039, WO2010076292, WO2010069742, WO2010069718, WO2010069957, WO2010057784, WO2010054986, WO2010018043, WO2010003783, WO2010003792, WO2011023716, WO2010142539, WO2010118959, WO2010115813, WO2010105942, WO2010105961, WO2010105962, WO2010094356, WO2010084203, WO2010078979, WO2010072456, WO2010069905, WO2010076165, WO2010072603, WO2010066486, WO2010066631, WO2010066632, WO2010063689, WO2010060821, WO2010049187, WO2010031607, or WO2010000636.

EXAMPLES

Example 1

A typical formulation is a high-shear T-granulate as produced e.g. in example 1 of WO 2004/003188 (Int'l Appl. No. PCT/DK03/000456) (containing enzyme, Na-sulfate, cellulose fibers, calcium carbonate and a binder, e.g. sucrose or dextrin) with the following formulation in the core (% by weight of uncoated dry granulate):

2% by weight Na-thiosulfate or 2% by weight methionine
5% by weight Magnesium sulfate heptahydrate
2% by weight Na-citrate dihydrate
0.5% by weight Citric acid monohydrate (to a pH in the enzyme concentrate feed of 4.5-5)

These stabilizers are preferably added to the aqueous enzyme concentrate before granulation.

After granulation and drying a 25% by weight (% by weight of dry uncoated granulate) Na-sulfate coating is applied under relatively humid condition (around 50% by weight RH in the outgoing air) in a fluid bed (e.g. as produced in example 4 of WO03/000456). A cosmetic and dust reducing outer thin film is further applied in fluid bed (e.g. PEG4000, kaolin and $TiO_2$).

The residual activity is based on wash performance analysis, i.e. 50% residual activity indicates that the washing performance after storage corresponds to that of unstored detergent with 50% dosage of the enzyme. After 1 week's storage at 37° C. and 70% by weight RH in a bleach containing detergent, the residual activity is typically less than 10% by weight if one of the stabilizing techniques are excluded, and typically >75% by weight if all four techniques are present. Wash performance is measured using a a mini-wash robot (60 ml wash solution) with a bleach containing detergent using a water hardness of 15° dH, wash at 40° C. in 30 minutes, detergent dosage 5 g/L and measure reflectance (460 nm on a Zeiss spectrophotometer) on rice starch based swatches (CS-28 from CFT of Holland)

Example 2

An amylase granulate is made with the following composition. The amounts are given in relation to the raw (uncoated) granulate. The granules are made by high shear granulation and coated by fluid bed coating

| Ingredient | Typical range (% w/w of total coated granule) |
|---|---|
| Core | |
| Cellulose fibers | 8% |
| Carbohydrate binder (e.g. dextrin and/or sucrose) | 5% |
| $Na_2SO_4$ | Add to 100% About 70% (excl. coating) |
| $CaCO_3$ (optional) | 0-5% |
| Na-thiosulfate or Methionine | 1.5% |
| Na-citrate | 1.5% |
| Citric acid | 0.4% |
| $MgSO_4 \cdot 7H_2O$ | 4% |
| Stainzyme enzyme concentrate | 1-3% (solids) |
| Coating | |
| Layer 1 | |
| $Na_2SO_4$ | 20-30% |
| Titan | 1% |
| Dextrin (optional) | 0-1% |
| Layer 2 | |
| Kaolin | 1% |
| PEG-4000 | 1% |

Example 3

A number of enzyme granulates were prepared by mixing enzyme and stabilizers as shown in the table below and granulating in a mixer. A salt coating and film coating were applied as indicated. Each granulate was then added to a granular bleach detergent and stored at 37° C., 70% relative humidity. The enzymes tested were two *Bacillus* amylase variants (denoted Amylase X and Y, respectively). Amounts are given as % by weight in relation to the weight of the core. The film coating was applied in an amount of 3% by weight of the core. The film coating consisted of Sepifilm LP030 (A mixture of Hypromellose (HPMC) as film forming polymer, Micro-Crystalline Cellulose (MCC) and Stearic acid).

The amylase granulates were produced as a high-shear T-granulate as in Example 2 of WO 2004/003188 (based on aqueous amylase concentrate, cellulose fibers and Na-sulfate as filler). After granulation and drying Na-sulfate coatings were applied (from a Na-sulfate solution) in a fluid bed.

The storage stability of the granulates was evaluated by determining the wash performance after 3 days and 7 days storage. The results are shown below (wash performance based storage stability data given in % residual activity as described above).

| ID | Enzyme | Stabilizers in core | Coating | Film coating 3% Sepifilm | Residual wash performance after storage 3 days | 7 days |
|---|---|---|---|---|---|---|
| A | Amylase X | 2% Na-thiosulfate 5% Mg-sulfate $7H_2O$ | 40% Na-sulfate | Yes | 60% | (<60%) |
| B | Amylase X | 2% citrate 0.5% citric acid 5% Mg-sulfate $7H_2O$ | 30% Na-sulfate | Yes | — | 40% |
| C | Amylase X | 2% citrate 0.5% citric acid | 30% Na-sulfate | Yes | — | 0% |
| D | Amylase X | 2% Na-thiosulfate 2% citrate 0.5% citric acid 5% Mg-sulfate $7H_2O$ | 25% Na-sulfate | Yes | 100% | 100% |
| E | Amylase Y | 2% Cysteine 2% citrate 0.5% citric acid 5% Mg-sulfate $7H_2O$ | 25% Na-sulfate | Yes | 100% | 100% |
| F | Amylase Y | 2% Na-thiosulfate 2% citrate 0.5% citric acid 5% Mg-sulfate $7H_2O$ | 25% Na-sulfate | Yes | 100% | 100% |
| G | Amylase Y | 2% Methionine 2% citrate 0.5% citric acid 5% Mg-sulfate $7H_2O$ | 25% Na-sulfate | No | 100% | 100% |
| H | Amylase Y | 2% citrate 0.5% citric acid 5% Mg-sulfate $7H_2O$ | 25% Na-sulfate | Yes | | 0% |

-continued

| ID | Enzyme | Stabilizers in core | Coating | Film coating 3% Sepifilm | Residual wash performance after storage 3 days | 7 days |
|---|---|---|---|---|---|---|
| I | Amylase Y | 2% Na-thiosulfate<br>2% citrate<br>0.5% citric acid<br>5% Mg-sulfate 7H$_2$O | None | No | | 2% |
| J | Amylase Y | 2% Cysteine<br>2% citrate<br>0.5% citric acid<br>5% Mg-sulfate 7H$_2$O | None | No | | 8% |
| K | Amylase Y | 0.5% Methionine<br>2% citrate<br>0.5% citric acid<br>5% Mg-sulfate 7H$_2$O | 25% Na-sulfate | No | | 85% |
| L | Amylase Y | 0.5% Methionine<br>2% citrate<br>0.5% citric acid<br>5% Mg-sulfate 7H$_2$O | 25% Na-sulfate<br>0.15% Fe—SO$_4$·7H$_2$O | No | | 100% |

The results demonstrate the synergistic effect of adding a reducing agent/antioxidant, a multivalent cation, a slight amount of acidic buffer, and applying a salt coating. Thus, a comparison of the results for granulates B and C shows the effect of adding a multivalent cation; a comparison of the results for granulates A and D shows the effect of adding a slight amount of acidic buffer; a comparison of the results for granulates B and D or comparing G and H with E and F shows the effect of adding a reducing agent/antioxidant; and a comparison of the results for granulates I and J with E and F shows the effect of applying a salt coating. Granulate G shows that the a very good stabilizing effect can be obtained also without the film coating. K and J show the effect of adding a peroxide decomposing catalyst to the salt coating.

Example 4

A Cellulase granulate was produced as a high-shear T-granulate as in example 2 of WO 2004/003188 (based on Cellulose fibers and Na-sulfate as filler) and including in the core the following stabilizers (% by weight of uncoated dry granulate):
2% Na-thiosulfate
5% Magnesium sulfate heptahydrate
2% Na-citrate dihydrate
0.5% Citric acid monohydrate (to a pH in the enzyme concentrate feed of 4.5-5) The stabilizers were added to the aqueous enzyme concentrate before granulation.

After granulation and drying a 27% by weight (% by weight of dry uncoated granulate) Na-sulfate:TiO$_2$ 25:2 w/w coating was applied (from a 25:2:73 Na-sulfate:TiO$_2$:water solution) in a fluid bed. A cosmetic and dust reducing outer thin film was further applied in fluid bed (2.5% PEG4000: TiO$_2$ 1:1 w/w).

A part of the uncoated granulate was wax-coated in a mixer with 8% melted PEG4000 and 14% TiO$_2$:Calcium carbonate 1:3 w/w Example 5 (Reference)

A Cellulase granulate was produced as a high-shear T-granulate as in Example 2 of WO 2004/003188 (based on Cellulose fibers and Na-sulfate as filler) without addition of stabilizers After granulation and drying a 27% by weight (% by weight of dry uncoated granulate) Na-sulfate:TiO$_2$ 25:2 w/w coating was applied (from a 25:2:73 Na-sulfate:TiO$_2$:water solution) in a fluid bed. A cosmetic and dust reducing outer thin film was further applied in fluid bed (2.5% PEG4000: TiO$_2$ 1:1 w/w).

A part of the uncoated granulate was coated in a mixer with 8% melted PEG4000 and 14% TiO$_2$:Calcium carbonate 1:3

The stability in a bleach containing detergent of the 4 granulates from example 4 and 5 was tested over 8 weeks at 37° C. and 55% relative humidity (residual activity measured by a standard cellulase assay):

| ID | Stabilizers in core | Coating | % residual activity |
|---|---|---|---|
| Ex. 4 salt coating | Yes | Na-sulfate | 70% |
| Ex. 4 wax coating | Yes | Wax | 3% |
| Ex. 5 salt coating | No | Na-sulfate | 28% |
| Ex. 5 wax coating | No | Wax | 7% |

It can be observed that adding the stabilizers for a wax coated granule actually decrease stability somewhat, while for a salt coated granulate adding the stabilizers significantly improve stability. The granulate with both stabilizers and salt coating is significantly better than the other samples.

Example 6

An alkaline protease granulate was produced as a high-shear T-granulate as in example 2 of WO 2004/003188 (based on spray-dried protease, Cellulose fibers and Na-sulfate as filler) with the following stabilizers in the core (% by weight of uncoated dry granulate):
0.7% Na-thiosulfate
5% Magnesium sulfate heptahydrate
2.1% Na-citrate dihydrate
0.5% Citric acid monohydrate The stabilizers were added to the granulation liquid (water) before granulation.

After granulation and drying a 27% by weight (% by weight of dry uncoated granulate) Na-sulfate:TiO$_2$:dextrin 25:1:1 w/w coating was applied (from a 25:1:1:73 Na-sulfate: TiO$_2$:dextrin:water solution) in a fluid bed. A cosmetic and dust reducing outer thin film was further applied in fluid bed (2.0% PEG4000:TiO$_2$:Kaolin 4:3:3 w/w).

Example 7 (Reference)

An alkaline protease granulate was produced as a high-shear T-granulate as in example 2 of WO 2004/003188 (based on spray-dried protease, Cellulose fibers and Na-sulfate as filler) with the following stabilizers in the core (% by weight of uncoated dry granulate):

0.7% Na-thiosulfate

The stabilizer was added to the granulation liquid (water) before granulation.

The uncoated granulate was coated in a mixer with 6% melted PEG4000 and 14% TiO$_2$:Calcium carbonate 1:1

The stability in a bleach containing detergent of the 2 granulates from example 6 and 7 were tested over 2 weeks at 37° C. and 70% relative humidity (residual activity measured by a standard protease assay):

| ID | Stabilizers in core | Coating | % residual activity |
|---|---|---|---|
| Ex. 6 salt coating | Yes | Na-sulfate | 91% |
| Ex. 7 wax coating | No | Wax | 16% |

The stabilizer mixture with salt coating significantly increases storage stability of the protease.

The invention claimed is:

1. A granule comprising a core and a protective coating, wherein:
    a) the core comprises an enzyme which is an amylase, a lipase, a protease, a cellulase, a mannanase, or a pectate lyase, and
    b) the core comprises a thiosulfate, cysteine, methionine or a transition metal salt in an amount of 0.1-10% by weight relative to the core, and
    c) the core comprises a salt of Mg or Zn cation in an amount of 0.1-15% by weight of the salt in anhydrous form relative to the core, and
    d) the core comprises an acidic buffer which is a mixture of citric acid and a citrate in an amount of 1-5% by weight relative to the core, and
    e) the coating comprises a salt, the salt coating making up 10-50% by weight relative to the core, and the salt coating comprising at least 75% by weight sodium sulfate.

2. The granule of claim 1, wherein the salt of a Mg or Zn cation is magnesium sulfate or zinc sulfate.

3. The granule of claim 1, wherein the salt in the coating has a constant humidity of at least 80% by weight.

4. The granule of claim 1, wherein the salt coating constitutes 10-30% by weight relative to the core.

5. The granule of claim 1, wherein:
    a) the enzyme is an amylase, a protease, a cellulase or a lipase,
    b) the core comprises Na-thiosulfate or methionine in an amount of 0.5-5% by weight relative to the core,
    c) the core comprises magnesium sulfate or zinc sulfate in an amount of 2-8% by weight of the core,
    d) the core comprises a mixture of citric acid and a citrate in an amount of 1-5% by weight relative to the core, and
    e) the salt coating makes up 10-30% by weight relative to the core, and comprises at least 75% by weight sodium sulfate.

6. The granule of claim 1 which further comprises an additional coating on the outside of the salt coating, wherein the additional coating comprises a film-forming agent.

7. A granular detergent composition comprising a surfactant and the granule of claim 1.

8. The detergent composition of claim 7 which further comprises a bleaching system comprising a H$_2$O$_2$ source.

9. The granule of claim 6, wherein the film-forming agent comprises polyethylene glycol, hydroxypropyl methyl cellulose (HPMC or MHPC), or polyvinyl alcohol (PVA).

10. The granule of claim 1, wherein the thiosulfate is Na-thiosulfate.

* * * * *